(12) United States Patent
Herrmann et al.

(10) Patent No.: US 8,500,329 B2
(45) Date of Patent: Aug. 6, 2013

(54) MEDICAL EXAMINATION OR TREATMENT DEVICE

(75) Inventors: Norbert Herrmann, Ebnath (DE); Andreas Limmer, Seybothenreuth (DE)

(73) Assignee: Siemens Aktiengesellschaft, München (DE)

( * ) Notice: Subject to any disclaimer, the term of this patent is extended or adjusted under 35 U.S.C. 154(b) by 58 days.

(21) Appl. No.: 13/215,925

(22) Filed: Aug. 23, 2011

(65) Prior Publication Data

US 2012/0219120 A1  Aug. 30, 2012

(30) Foreign Application Priority Data

Aug. 25, 2010  (DE) .......................... 10 2010 035 394

(51) Int. Cl.
*H05G 1/02* (2006.01)
(52) U.S. Cl.
USPC ........................................................ 378/197
(58) Field of Classification Search
USPC .......................................... 378/196, 197, 198
See application file for complete search history.

(56) References Cited

U.S. PATENT DOCUMENTS

| 6,609,826 B1 | 8/2003 | Fujii et al. |
| 2006/0062347 A1* | 3/2006 | Nekovar et al. .................... 378/4 |
| 2011/0243309 A1* | 10/2011 | Weijiang ....................... 378/197 |
| 2012/0289821 A1* | 11/2012 | Graumann et al. ............. 378/19 |

FOREIGN PATENT DOCUMENTS

DE  602 07 625 T2  8/2006

OTHER PUBLICATIONS

German Office Action dated Jun. 3, 2011 for corresponding German Patent Application No. DE 10 2010 035 394.9 with English translation.

* cited by examiner

*Primary Examiner* — Glen Kao
(74) *Attorney, Agent, or Firm* — Lempia Summerfield Katz LLC

(57) ABSTRACT

A medical examination or treatment device including a C-arm operable to be moved along a trajectory on a holder is provided. First magnet elements or magnetic field generation elements are provided on the C-arm, and second magnetic field generation elements are provided on the holder. The first magnet elements or magnetic field generation elements and the second magnetic field generation elements interact with one another to establish a magnetic field guiding the C-arm in a non-contact manner. The magnetic field moves the C-arm along the trajectory.

20 Claims, 2 Drawing Sheets

MEDICAL EXAMINATION OR TREATMENT DEVICE

This application claims the benefit of DE 10 2010 035 394.9, filed Aug. 25, 2010.

BACKGROUND

The present embodiments relate to a medical examination or treatment device including a C-arm that is guided on a holder to allow movement along a trajectory.

Medical examination or treatment devices include X-ray devices, in which a radiation source is arranged at one end of a C-arm, and a radiation detector is arranged at the other end of the C-arm. Since the C-arm is guided so that the C-arm is movable along a trajectory, the C-arm may be moved together with the imaging device relative to a patient around an isocenter. A motor drive (e.g., a motor-driven driveshaft that engages with a belt that is connected to the C-arm) is used to move the C-arm. When the belt moves, the result is a movement of the C-arm otherwise guided via rollers or like devices.

Because of the significant weight of the C-arm along with the components installed on the C-arm, the motor is to be dimensioned to a significant capacity, since the C-arm moves the entire mass. Since very fast rotations may be performed with such devices, the aim is to achieve high accelerations, which is to be taken into account in the design of the motor.

SUMMARY AND DESCRIPTION

The present embodiments may obviate one or more of the drawbacks or limitations in the related art. For example, a medical examination or treatment device having an improved drive concept may be provided.

In one embodiment, magnet elements may be provided on the C-arm, and magnetic field generation elements may be provided on the holder. The magnet elements and the magnetic field generation elements may interact with one another and set up a magnetic field that guides the C-arm in a non-contact manner and moves C-arm along a trajectory.

In one embodiment of an examination or treatment device, the C-arm is guided and moved via a magnetic levitation system. The C-arm, for example, forms an armature that is movably guided on a stator (e.g., the holder). The magnet elements are provided on the C-arm, and the magnetic field generation elements are provided on the holder arm. A magnetic field is established between the magnet elements and the magnetic field generation elements for movement and guidance. The C-arm is guided by the magnetic field in a non-contact manner on the holder (e.g., even during the movement). No mechanical contact is made between the C-arm and the holder during the movement. This leads to an almost completely silent movement of the C-arm along the holder. No or little friction losses occur compared to corresponding mechanical guides in the prior art that, with respect to the significant rotational speeds, are to be designed for the corresponding accelerations and consequently, are subjected to the corresponding wear. In addition, the use of the magnetic levitation guide allows an accurate positioning of the C-arm relative to the holder (e.g., the C-arm may be moved to desired positions with very high precision, and the traveling field generated on the magnetic field generation elements side, because of very close interaction with the magnetic elements on the C-arm, allows high accelerations and speeds to be achieved).

A plurality of permanent magnets distributed over the length of the C-arm may be provided as magnetic elements on the C-arm. In one embodiment, a plurality of electromagnets is provided as magnetic field generation elements on the holder. Viewed vertically, the plurality of electromagnets is arranged distributed over the length of the holder, and the plurality of electromagnets may be supplied with power separately. This leads to a traveling magnetic field that may be generated over the length of the holder (e.g., over the length of an interaction zone between the elements along the electromagnets by corresponding activation of the magnets). The traveling field possesses a movement component that is transmitted as a result of the alternating field effect at the magnetic elements provided on the arm side (e.g., permanent magnets), via which the movement vector is transmitted to the C-arm.

With respect to construction, two slots may, for example, be provided on opposite sides of the holder. A corresponding limb of the C-arm, which is C-shaped in cross-section, may penetrate each of the two slots. A plurality of magnetic elements (e.g., permanent magnets) may be provided on opposite sides of each limb, and a plurality of magnetic field generation elements (e.g., electromagnets) may be provided on opposite slot walls. In one embodiment, two limbs of the C-arm are accommodated in respective holder-side slots (e.g., each arm is encompassed by two opposite slot walls). The magnetic elements and the magnetic field generation elements are arranged such that a magnet element and a magnetic field generation element are opposite each other in each case. For each limb of the C-arm, viewed in the horizontal plane, two magnet elements and two magnetic field generation elements (e.g., permanent magnets and electromagnets) lie opposite one another. The electromagnets are, for example, a carrier magnet or a exciter magnet with corresponding linear generation windings, via which the magnetic fields effecting the levitation and movement are generated. As a consequence of the opposing arrangement of the respective pairs of permanent magnet and electromagnet in accordance with this embodiment, it is sufficient for a movement for the traveling field to be generated only via the electromagnets provided on one side of the holder. It is advantageous, however, for the electromagnets lying opposite one another in each case to be activated synchronously in order to almost generate a duplicated two-sided traveling field. As a consequence of the mirror-symmetrical design, four pairs of magnet elements and magnetic field generation elements are realized opposite one another so that, when supplied with power, all four essentially identical electromagnets produce four traveling fields.

In order to not have to supply the electromagnets continuously with power, so that the C-arm remains in a non-contact position relative to the holder, a plurality of slide or roller elements may be provided on the C-arm. The plurality of slide or roller elements at least supports the C-arm in a stationary state. When the device is not in operation and consequently the electromagnets are not supplied with power and no magnetic fields are being generated, the C-arm rests on corresponding slide or roller elements.

The slide or roller elements may be arranged on a base limb of the C-shaped C-arm. The slide or roller elements extend over at least a part of the length of the C-shaped C-arm. Lying opposite the slide or roller elements, further slide or roller elements interacting with the slide or roller elements are provided on the holder. Corresponding slide or roller elements are provided on circumferential or radially-opposite main surfaces of the base limb and/or the holder, respectively, lying opposite one another. The C-arm rests on the further slide or roller elements when the C-arm is not being held in a non-contact manner via the magnetic fields on the holder. The further slide or roller elements may come into contact with the C-arm temporarily and if the C-arm is not moving. This leads to slide or roller elements not being subjected to any wear.

In one embodiment, the slide or roller elements provided on the base limb and the slide or roller elements in the holder (e.g., assigned to the slide or roller elements provided on the base limb) are arranged in two parallel rows, which eliminates tilting.

In order to further realize secure lateral guidance, in one embodiment, slide, roller or guide elements are provided on floor surfaces of the two slots, and face surfaces of the C-arm limbs are provided with slide, roller or guide elements interacting with the slide, roller or guide elements provided on the floor surfaces. For surfaces of the limbs and of the slots adjoining each other with a lateral offset, slide, roller or guide elements are provided that provide secure lateral guidance and simultaneously, are not subject to any wear. The guide elements may interact magnetically with each other, so that as a result of the repelling forces to both sides, a central position is maintained. In such cases, the guide elements may be designed as guide rails arranged on the limb of the C-arm and as magnetic elements arranged on the slot floor (e.g., permanent magnets).

In one embodiment, a mechanical brake device for fixing the C-arm in a stationary position may be provided. Using the mechanical brake device, the C-arm is prevented from moving on its own if, for example, a person knocks into the arm or if the arm is designed non-symmetrically with regard to load distribution. A balanced distribution of weight of the C-arm is not required for the present embodiments, since the respective position may easily be fixed in operation via the interacting magnetic fields and when not in operation, by using the corresponding braking device.

DETAILED DESCRIPTION OF THE DRAWINGS

Figure 1:
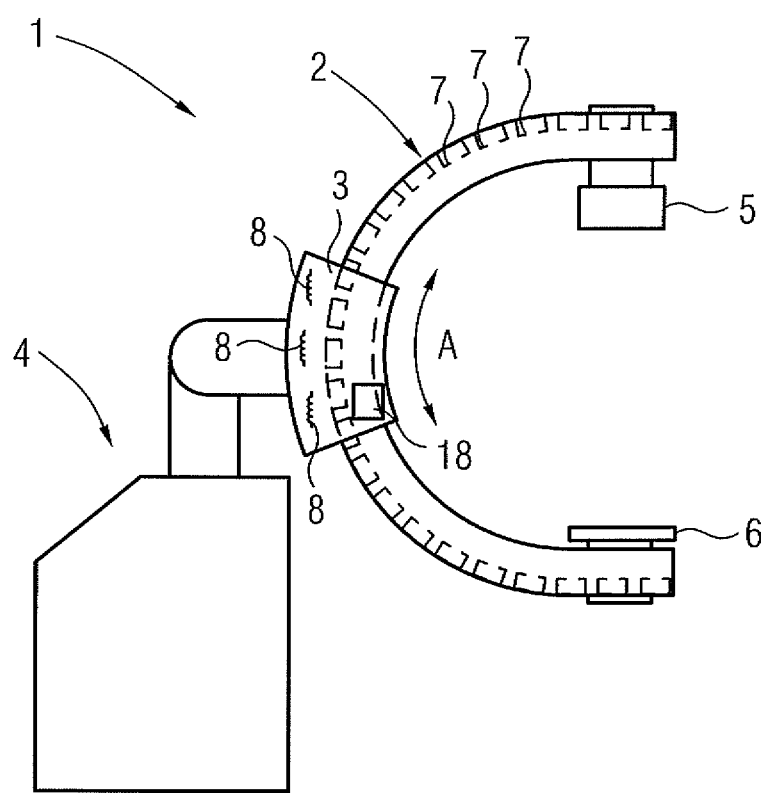
FIG. 1 shows one embodiment of an examination or treatment device.

FIG. 1 shows a basic diagram of one embodiment of a medical examination or treatment device 1 that includes a C-arm 2 and a holder 3. In the example shown in FIG. 1, the medical examination or treatment device 1 is accommodated on a floor stand 4 allowing vertical and horizontal adjustment. In another embodiment, the C-arm 2 may be arranged in a ceiling mount.

A radiation source 5 and a radiation detector 6 are arranged on the C-arm 2 in order to enable radioscopy images (e.g., X-ray images) to be recorded. The C-arm 2 is arranged for movement along the holder 3 (e.g., as indicated by arrow A). The C-arm may be stationary during operation.

In order to move the C-arm 2 along the holder 3, magnet elements 7 (e.g., in the form of individual permanent magnets) that are arranged on or in an area of an outer circumference are arranged on the C-arm 2. Magnetic field generation elements 8 (e.g., in the form of individual electromagnets) are arranged on the holder 3. The electromagnets 8 serve as carrier or exciter magnets for generating a magnetic field that interacts with the permanent magnets 7. The electromagnets 8 may be controlled separately and are arranged on the holder 3 linearly behind one another in relation to the direction of movement of the C-arm 2, so that for corresponding alternate activation of the individual electromagnets 8, a moving magnetic field moving along the holder 3 is produced. The moving magnetic field interacts with the permanent magnets 7 so that the permanent magnets 7 follow the moving magnetic field, and consequently, a movement of the C-arm 2 is produced.

Figure 2:
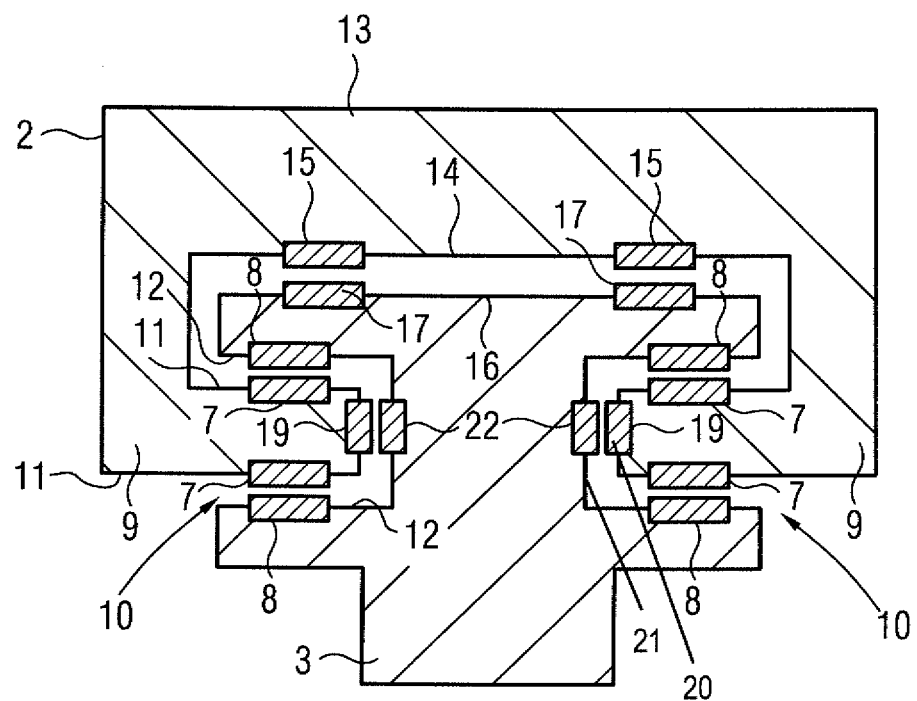
FIG. 2 shows a side view of a cross-section of one embodiment of the examination or treatment device from FIG. 1.

FIG. 2 shows a detailed diagram structure of one embodiment of a magnetic field levitation system. FIG. 2 shows the C-arm 2 and the holder 3. Viewed in cross-section, the C-arm 2 has a C-shaped cross-section. The C-arm 2 includes two limbs 9 pointing towards each other.

The holder 3 has two slots 10 opposite one another opened in opposing directions. A respective limb 9 penetrates into (e.g., is disposed in) each of the two slots 10.

Two of the magnet elements 7 (e.g., the permanent magnets) are arranged on two opposing lateral surfaces 11 of the respective limb 9. Two of the magnetic field generation elements 8 (e.g., the electromagnets) are provided opposite the two magnet elements 7 on respective neighboring slot walls 12. Two pairs including respective first and second magnetic field generation elements are provided per side.

Slide or roller elements 15 (e.g., lubricant-coated slide rails or slide rails made of polytetrafluoroethylene (PTFE)) are provided on a radial outer circumferential surface 14 of a base limb 13 of the C-arm 2, pointing towards the holder 3. Further slide or roller elements 17 (e.g., roller guides and/or like devices) are provided on an opposing surface 16 of the holder 3. The slide or roller elements 15, 17 serve to support the C-arm 2 if no magnetic fields are established via the magnet elements 7 and the magnetic field generation elements 8 or the magnet elements 7 and the magnetic field generation elements 8 are not interacting (i.e., the C-arm 2 is not supported in a non-contact manner on the holder 3, but the magnetic levitation device is switched off). The C-arm 2 rests with the slide or roller elements 15 on the slide or roller elements 17 (e.g., the C-arm 2 does not move). This is because the C-arm 2 is fixed in a rest position via a braking device 18 not shown in any greater detail in FIG. 2 (e.g., shown by way of example in FIG. 1). The slide or roller elements 15 and 17 may not be subject to any wear, since the slide or roller elements 15 and 17 do not interact during the movement of the C-arm 2.

For lateral guidance, slide, roller or guide elements 20 are arranged on face sides 19 of the two limbs 9. Slide, roller or guide elements 22 are arranged on opposite floor surfaces 21 of the two slots 10. The slide, roller or guide elements 20, 22 may include rollers or slide rails. In one embodiment, elements acting magnetically with each other are used (e.g., guide rails 20 made of a material interacting accordingly with the elements 22 embodied as guide magnets). The overall result, as a consequence of the magnetic interaction, is that the elements 20 are repelled from the elements 22, so that the C-arm 2 is securely guided and spaced laterally.

During operation, the electromagnets 8, which may include a laminated core with three-phase AC windings inserted into slots, generate corresponding magnetic fields that "move" on corresponding activation of the electromagnets 8 over the electromagnets 8 connected downstream from one another. A movement of a field along the holder 3 thus starts. As a result of the interaction with the opposing permanent magnets 7 in each case, the permanent magnets 7, because of magnetic attraction or repulsion (depending on polarity of the permanent magnets 7 relative to the field direction) follow the moving magnetic fields so that the C-arm 2 moves as a result. The principle of this levitation technique is similar to a three-phase AC or linear motor, with in effect two such three-phase AC or linear motors, for example, being installed per side.

One embodiment of an integrated magnetic levitation device that includes the magnet elements 7 and the magnetic field generation elements 8 allows a non-contact, completely or essentially silent movement and guidance of the C-arm 2 on or along the holder 3. The lateral guidance and secure fixing of the C-arm 2 when magnetic operation is switched off by the slide or roller elements 15 and 17 is provided by the corresponding side guide elements (e.g., in the form of the slide, roller or guide elements 20, 22) in conjunction with the braking device 18.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A medical examination or treatment device comprising:
   a C-arm operable to be moved along a trajectory and guided on a holder;
   magnet elements provided on the C-arm; and
   magnetic field generation elements provided on the holder,
   wherein the magnet elements and the magnetic field generation elements interact to establish a moving magnetic field, and
   wherein the moving magnetic field guides the C-arm in a non-contact manner and moves the C-arm along the trajectory.

2. The examination or treatment device as claimed in claim 1, wherein the magnet elements comprise a plurality of permanent magnets that is arranged on the C-arm distributed over a length of the C-arm, and
   wherein the magnetic field generation elements comprise a plurality of electromagnets provided on the holder.

3. The examination or treatment device as claimed in claim 1, wherein two slots are provided on opposite sides of the holder,
   wherein limbs of the C-arm, which has a C-shaped cross section, engage the two slots,
   wherein at least some of the magnet elements are provided on each of the limbs on opposite sides, and
   wherein at least some of the magnetic field generation elements are provided on opposing slot walls.

4. The examination or treatment device as claimed in claim 1, further comprising a plurality of slide or roller elements provided on the C-arm and the holder, the plurality of slide or roller elements supporting the C-arm in at least a stationary state.

5. The examination or treatment device as claimed in claim 3, wherein the C-shaped C-arm comprises a base limb, on which first slide or roller elements are provided over at least a part of a length of the base limb, and
   wherein second slide or roller elements are provided on the holder, opposite the first slide or roller elements, the second slide or roller elements interacting with the first slide or roller elements.

6. The examination or treatment device as claimed in claim 5, wherein the first slide or roller elements provided on the base limb and the second slide or roller elements assigned to the first slide or roller elements arranged on the holder are arranged in two parallel rows.

7. The examination or treatment device as claimed in claim 5, further comprising:
   third slide, roller or guide elements provided on floor surfaces of the two slots; and
   fourth slide, roller or guide elements interacting with the third slide, roller or guide elements, the fourth slide, roller or guide elements being provided on face sides of the C-arm limbs.

8. The examination or treatment device as claimed in claim 7, wherein the third slide, roller or guide elements interact magnetically with the fourth slide, roller or guide elements.

9. The examination or treatment device as claimed in claim 8, wherein the third slide, roller or guide elements comprise magnet elements arranged on the floor surfaces, and
   wherein the fourth slide, roller or guide elements comprise guide rails arranged on the C-arm limbs.

10. The examination or treatment device as claimed in claim 1, further comprising a mechanical brake device configured to fix the C-arm when the C-arm is stationary.

11. The examination or treatment device as claimed in claim 2, wherein two slots are provided on opposite sides of the holder,
    wherein limbs of the C-arm, which has a C-shaped cross section, engage the two slots,
    wherein at least some permanent magnets of the plurality of permanent magnets are provided on each of the limbs on opposite sides, and
    wherein at least some electromagnets of the plurality of electromagnets are provided on opposing slot walls.

12. The examination or treatment device as claimed in claim 2, further comprising a plurality of slide or roller elements provided on the C-arm and the holder, the plurality of slide or roller elements supporting the C-arm in at least a stationary state.

13. The examination or treatment device as claimed in claim 3, further comprising a plurality of slide or roller elements provided on the C-arm and the holder, the plurality of slide or roller elements supporting the C-arm in at least a stationary state.

14. The examination or treatment device as claimed in claim 5, further comprising:
    third slide, roller or guide elements provided on floor surfaces of the two slots; and
    fourth slide, roller or guide elements interacting with the third slide, roller or guide elements, the fourth slide, roller or guide elements being provided on face sides of the C-arm limbs.

15. The examination or treatment device as claimed in claim 6, further comprising:
    third slide, roller or guide elements provided on floor surfaces of the two slots; and
    fourth slide, roller or guide elements interacting with the third slide, roller or guide elements, the fourth slide, roller or guide elements being provided on face sides of the C-arm limbs.

16. The examination or treatment device as claimed in claim 2, further comprising a mechanical brake device configured to fix the C-arm when the C-arm is stationary.

17. The examination or treatment device as claimed in claim 3, further comprising a mechanical brake device configured to fix the C-arm when the C-arm is stationary.

18. The examination or treatment device as claimed in claim 4, further comprising a mechanical brake device configured to fix the C-arm when the C-arm is stationary.

19. The examination or treatment device as claimed in claim 6, further comprising a mechanical brake device configured to fix the C-arm when the C-arm is stationary.

20. The examination or treatment device as claimed in claim 8, further comprising a mechanical brake device configured to fix the C-arm when the C-arm is stationary.

* * * * *